United States Patent [19]
Raible

[11] Patent Number: 6,162,017
[45] Date of Patent: Dec. 19, 2000

[54] BLOOD PUMP

[75] Inventor: Donald A. Raible, Santa Ana, Calif.

[73] Assignee: Cardiovascular Innovations LLC, Clovis, Calif.

[21] Appl. No.: 09/290,863

[22] Filed: Apr. 14, 1999

[51] Int. Cl.[7] .................................................. F01D 1/02
[52] U.S. Cl. ........................................ 415/206; 415/900
[58] Field of Search ............................. 415/72, 74, 143, 415/199.6, 206, 214.1, 900; 417/360, 423.1, 423.14; 248/121, 125.1, 230.1, 230.2, 231.31

[56] References Cited

U.S. PATENT DOCUMENTS

| | | | |
|---|---|---|---|
| 3,249,057 | 5/1966 | Callahan | 415/206 |
| 5,360,317 | 11/1994 | Clausen et al. | 415/206 |
| 5,400,991 | 3/1995 | Werner | 248/230.2 |
| 5,411,706 | 5/1995 | Hubbard et al. | 417/423.14 |
| 5,501,574 | 3/1996 | Raible | 415/900 |

*Primary Examiner*—Edward K. Look
*Assistant Examiner*—Hermes Rodriguez
*Attorney, Agent, or Firm*—William E. Mouzavires

[57] ABSTRACT

A stand alone blood pump which can be used with different types of oxygenators or extra corporeal circuits during surgery. After use the pump is easily detachable from its drive motor to enable a new blood pump to be mounted for the next operation. The pump impeller includes vanes at the base which extend at an angle to the plane of rotation and smoothly merge along a common plane with a plurality of helical fingers respectively. The width of the helical fingers gradually diminishes from the vanes to their extremities which are angularly spaced from each other at the pump inlet. The helical fingers flow the blood helically about the impeller axis to the vanes which then centrifugally flow the blood to the pump outlet tangentially of the pump housing.

23 Claims, 2 Drawing Sheets

BLOOD PUMP

BACKGROUND OF INVENTION

The present invention generally relates to liquid pumps and more specifically to blood pumps used for example in open-heart surgery or cardiovascular procedures. The blood pump of the present invention is of the same general type of blood pump invented by me and disclosed in U.S. Pat. No. 5,368,438 and No. 5,501,574. However the blood pump of the present invention incorporates highly useful and novel improvements over the aforementioned blood pump as well as others of the prior art.

OBJECTS OF THE PRESENT INVENTION

An object of the present invention is to provide a novel and improved blood pump that may be used with different types of oxygenators, reservoirs, filters or other extracorporeal equipment.

A further object of the present invention is to provide a novel blood pump that provides improved blood flow through the pump to avoid damage to the blood. Another object is to provide such a blood pump requiring only a minimum blood-prime.

Another object of the present invention is to provide a blood pump having a novel housing for accommodating a direct mechanical driving system by use of direct coupling to the motor for driving the pump.

Another object of the present invention is to provide a novel and improved impeller for a blood pump that provides improved blood flow to avoid damage to the blood.

A still further object of the present invention is to provide a blood pump capable of operating with low flow rates as well as high flow rates.

SUMMARY OF THE PRESENT INVENTION

One aspect of the present invention is realized by providing a disposable blood pump with a novel housing that attaches to a reusable direct drive motor so that the pump and the motor stand alone as a unit that may be connected to any type of oxygenator or extracorporeal circuit. The pump is easily detachable from the direct drive motor after use, and a new blood pump is attached for the next operation. The pump connected to the extracorporeal circuit can be disconnected from the direct motor drive and connected to another direct motor drive without disturbing the blood within the circuit.

In addition, the present invention provides a novel impeller that generates helical and centrifugal blood flow with a smooth and uninterrupted transition between the helical and centrifugal flow. In addition, the impeller includes a plurality of equi-angularly spaced blades or vanes at its base for generating the centrifugal flow and a plurality of fingers extending helically and upwardly from the vanes for generating the helical flow along and about out the axis of the impeller. This helical portion of the impeller gently starts the blood to rotate and smoothly feeds the centrifugal portion of the impeller which generates the pressure and blood flow. The width of the helical fingers gradually diminishes from the vanes to the extremities of the fingers at the inlet end of the pump. In the preferred embodiment the pump housing is provided with inlet and outlet connectors for connecting the pump to standard tubing for connection from the patient/venous reservoir and to the oxygenator or extracorporeal circuit respectively.

DRAWINGS

Other objects and advantages of the present invention will become apparent from the following more detailed description taken in conjunction with the attached drawings in which.

DETAILED DESCRIPTION

Figure 1:
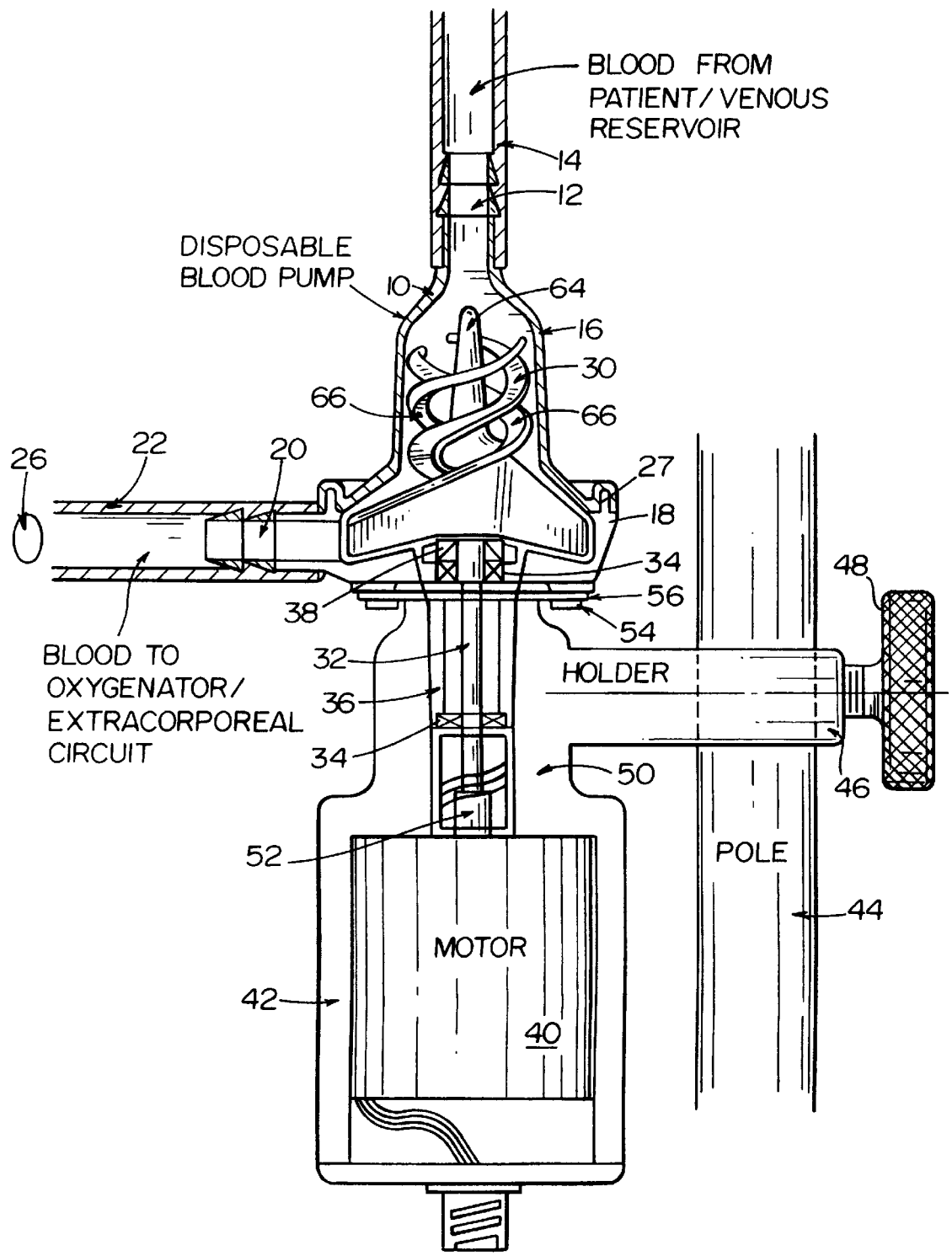
FIG. 1 is an elevational view of a blood pump and its associated direct motor drive system constituting a preferred embodiment of the present invention.

Referring now to the drawings in detail there is shown for illustrative purposes only a blood pump representing a preferred embodiment of the present invention. It includes a housing generally designated 10 having an inlet connector 12 at its upper end for connection to a standard tube 14 leading from, for example, a venus reservoir (not shown). Housing 10 further includes a bell-shaped intermediate section 16 and a base section 18 which closes the flanged bottom of the intermediate section 16. Base section 18 has an outlet connector 20 for receiving standard tubing 22 which leads to an oxygenator/extracorporeal circuit shown schematically at 26. Housing sections 16 and 18 may be sealed and secured to each other in any suitable manner such as by a circular flange 27 received in a complementary groove and urethane adhesive bonded or by other appropriate methods. The housing sections 16, 18 are molded from any suitable plastic such as polycarbonate transparent plastic.

Blood is pumped from the inlet 12 to the outlet 20 by an impeller generally designated 30 which flows the blood helically from inlet 12 along the housing section 16 about the axis of the impeller and then centrifugally outwardly to the outlet 20 as will be described in greater detail below. The lower end of impeller 30 has a drive shaft 32 mounted for rotation in bearings 34 received in a lower cylindrical housing portion 36 at upper and lower locations as indicated in FIG. 1. A seal 38 is provided about drive shaft 32 under the centrifugal portion of the impeller and above the top bearing 34. Impeller 30 is driven counterclockwise as shown in the drawings by any suitable drive motor shown as an electric motor 40 mounted in a housing generally designated 42 which in use is fixed to a stationary support shown as pole 44. In the specific embodiment shown, motor housing 42 has an arm 46 including a passage receiving support pole 44, and a thumb screw 48 engagable with the pole to secure the drive motor housing in place. The upper end of the drive motor housing 42 as shown in FIG. 1 has a hollow stem 50 which receives housing section 36 including the output shaft 32 of the disposable blood pump. Drive shaft 32 of the impeller extends through the interior of housing portion 36 of disposable blood pump and connects to the output shaft 52 of the drive motor to be driven thereby.

The blood pump is releasably secured to the stem 50 of the drive motor housing in any suitable manner to permit the blood pump to be secured then removed and disposed of after a surgical procedure. A new blood pump may then be easily mounted to the drive motor for the next operation. In the specific embodiment shown the lower housing section 18 has locking tabs extending from the bottom which with a twist of the blood pump securely connect the pump to the drive motor 40 as shown in FIG. 1. The bottom wall of the housing section 18 is provided with preferably three equi-angularly spaced locking tabs 54 for receiving a locking plate 56 fixed at the top of stem 50 to extend between tabs 54 and the bottom surface of housing section 18. Locking tabs 54 and plate 56 are engaged by first inserting the locking tabs 54 through the openings in plate 56, axially aligning the pump housing and the drive motor housing, and then rotating the housing clockwise relative to each other until the tabs are engaged by portions of the locking plate 56. Any other suitable releasable attachment means may be employed.

Figure 3:
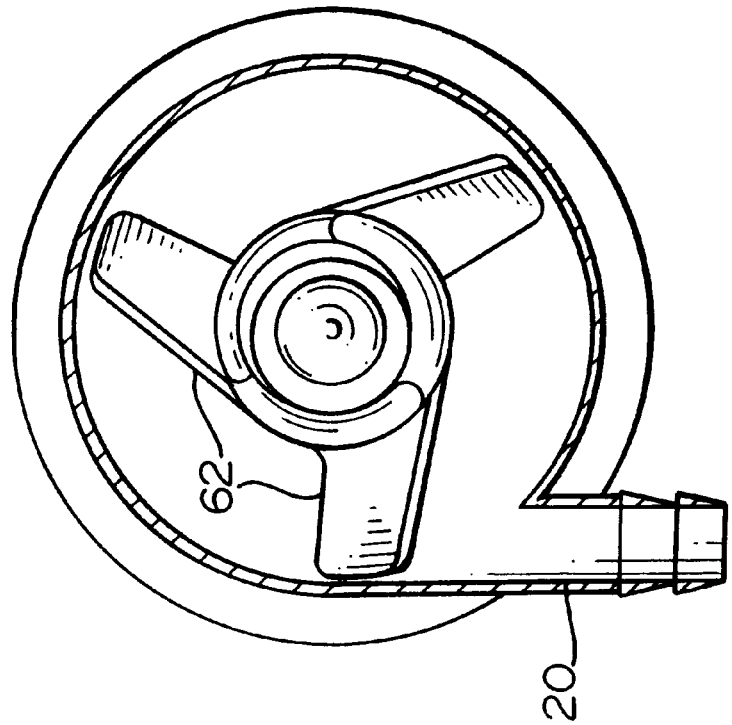
FIG. 3 is a plan view of the blood pump with parts removed.
Figure 2:
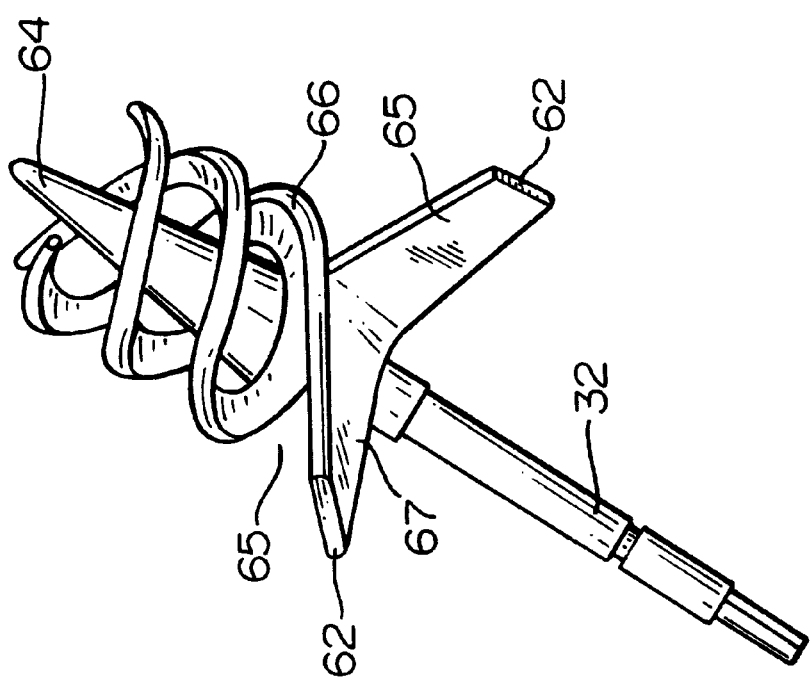
FIG. 2 is a perspective view of an impeller included in the blood pump.

The impeller 30 has a novel configuration which improves the blood flow to avoid damage to the blood. At the base of the impeller 30 are three equiangularly spaced vanes 62 projecting outwardly from a central conical shaped core pin 64. Vanes 62 as shown in FIG. 2 are generally planar at their top surfaces 65 and extend at an angle of about forty-five degrees (45°) relative to their plane of rotation. In the preferred embodiment vanes 62 extend generally tangentially from the core pin 64 and have an appropriate width of 0.400 inches adjacent to the core 64 and an approximate length from core pin 64 of 1.250 inches. In addition, the width of the vanes 62 decreases from the core 64 to their extremities, and the lower surfaces 67 of vanes 62 are slightly concave in the preferred embodiment and are tangential to helical fingers 66. In use vanes 62 move the blood in a circular path and out through the outlet 20 aided by centrifugal forces. To facilitate exit of the blood, outlet 20 extends tangentially from the base section 18 of the housing as shown in FIG. 3.

Vanes 62 respectively merge into three fingers 66 which extend helically about the core pin 64 from the vanes 62 to the top of core pin 64 at the inlet end of the pump housing. The merger takes place in the same plane and without interruption at the top surfaces of the vanes 62 and helical fingers 66. The width of helical fingers 66 gradually diminishes from the vanes 62 to the free ends of the fingers where they terminate in extremities. In the preferred embodiment the width of the helical fingers varies from 0.280 inches at the core 64 to 0.110 inches at their extremities. The spacing between the fingers 66 at the inlet provide a reduced area of contact with the blood entering the inlet of the housing section 16 to thus promote smooth and gentle flow of the blood onto the pump impeller entering housing section 16. As the blood is helically flowed by the fingers downwardly along the housing, the velocity of the blood flow gradually increases. The opposite edges of the fingers 66 are rounded to further promote smooth and gentle blood flow to the vanes 62. The flow of blood from the fingers 66 to the vanes 62 and then the outlet 20 is also effected smoothly and gently due to the smooth continuous transition between the fingers 66 and vanes 62 as well as the shape and orientation of the vanes 62. This shape also increases the effective length of the vanes at their lower surfaces 67 thus providing more displacement volume of blood to the outlet 20.

In the preferred embodiment, the impeller 30 is injection molded from a carbon fiber reinforced plastic on to a stainless steel shaft which extends into the core pin 64. The core pin 64 is tapered as shown in the drawings. Any other suitable material and manufacturing process may be used.

In use, the blood pump is mounted to the drive motor through the locking tabs 54 of the disposable blood pump and locking plate 56 of the drive motor housing. Standard size tubing 14 and 22 is applied to connect inlet connector 12 to a venous reservoir and outlet connector 20 to any type of oxygenator or extra corporeal circuit shown at 26. During operation of the pump, blood will freely flow into the housing at the top end unrestricted by the impeller. The extremities of the impeller fingers 66 will engage the blood and begin to move it about the axis of the impeller and as the blood progresses in its downward travel it will gradually increase in velocity as it moves helically and comes into progressive contact with the centrifugal impeller vanes. When it reaches the bottom of the housing the blood will flow onto transition surfaces 65, 67 of the vanes 62 (see FIG. 2) and into the space between the vanes 62 where the bottom surfaces 67 of the vanes 62 will drive the blood tangentially in a counter clockwise rotation out of the housing through outlet connector 20. At the conclusion of the operation, the blood pump is detached from the drive motor by a counterclockwise rotation, removed and disposed of. However, the drive motor may be reused with a new disposable blood pump.

It will therefore be seen that the blood pump of the present invention may be easily used in any type of an oxygenator or cardiovascular extracorporeal circuit since it is not incorporated into the latter but rather is connected to them with standard tubing. In addition the blood pump of the present invention is easily attached and detachable to and from the drive motor which may be reused in subsequent operations with new blood pumps. Moreover the blood pump of the present invention provides smooth and gentle blood flow avoiding damage to the blood due to the improved impeller and has a very low priming volume approximately 30 cc.

Although one preferred embodiment of the present invention has been shown and described, it will be readily apparent that obvious modifications to the invention may be made without departing from the invention the scope of which is defined in the appended claims.

I claim:

1. A blood pump comprising in combination; a housing including a blood inlet and a blood outlet, an impeller mounted for rotation in the housing for pumping blood from the inlet to the outlet, a drive motor for driving the impeller and having a drive shaft connected to the impeller and means on said housing releasably mounting the housing to the drive motor including interengagable locking members for securing the pump housing to the drive motor upon movement of the blood pump relative to the motor.

2. The blood pump defined in claim 1 wherein the outlet extends generally tangentially from the housing at a lower portion of the impeller.

3. The blood pump defined in claim 1 wherein said housing has an extension, said impeller having a drive shaft received in said extension and connected to said drive motor, said drive motor having a housing receiving said extension.

4. The blood pump defined in claim 1 wherein said motor includes a housing having a passage for mounting the motor and blood pump on a support received in said passage.

5. A blood pump including a housing, a blood inlet and a blood outlet communicating with the interior of the housing, an impeller for pumping blood from the inlet to the outlet, said Impeller including a centrifugal pumping section including a plurality of outwardly extending vanes rotatable in a plane for centrifugal pumping of blood to the outlet, said vanes including generally planar sections extending at an angle to said plane of rotation, said impeller further including a helical pumping section including a plurality of fingers extending from said vanes respectively along helical paths about the axis of the impeller and towards the inlet and terminating in extremities angularly spaced from each other at the inlet, and wherein said vanes merge into said fingers in a plane common to both and without interruption.

6. The blood pump defined in claim 5 wherein said fingers gradually diminish in width from said vanes to said extremities of said fingers.

7. The blood pump defined in claim 6 including three vanes merging into three fingers respectively.

8. The blood pump defined in claim 6 wherein outer and inner edge portions of said fingers are convexly rounded in cross-section.

9. The blood pump defined in claim 6 wherein the width of said fingers diminishes from 0.280 inches adjacent said vanes to 0.110 inches at the extremities.

10. The blood pump defined in claim 5 wherein said outlet extends tangentially from the housing at a level adjacent to said vanes.

11. The blood pump defined in claim 10 including a drive motor for driving the impeller, and means releasably securing the drive motor to the pump housing.

12. The blood pump defined in claim 11 wherein said housing has a bottom wall for receiving said drive motor.

13. An impeller for a blood pump having an inlet and an outlet, the impeller comprising in combination; a centrifugal pumping section including a plurality of outwardly extending vanes rotatable in a plane for centrifugal pumping of blood to an outlet of a blood pump, said vanes including generally planar sections extending at an angle to said plane of rotation, said impeller further including a helical pumping section including a plurality of fingers extending from said vanes respectively along helical paths towards the inlet and terminating in extremities angularly spaced from each other at the inlet, and wherein said blades merge into said fingers in a plane common to both and without interruption.

14. The impeller defined in claim 13 wherein said fingers gradually diminish in width from said vanes to said extremities of said fingers.

15. The impeller defined in claim 14 including three vanes merging into three fingers respectively.

16. The impeller defined in claim 14 wherein outer and inner edge portions of said fingers are convexly rounded in cross-section.

17. The impeller defined in claim 13 wherein said vanes extend at an angle of about forty-five degrees (45°) relative to their plane of rotation.

18. The impeller defined in claim 13 further including a central core and wherein said vanes extend generally tangentially outwardly from the core.

19. The blood pump defined in claim 2 wherein said impeller includes a central core and vanes extending generally tangentially from the core at the level of the outlet for moving blood to the outlet.

20. In combination with the blood pump defined in claim 1, an oxygenator spaced from said blood pump in a structure separate from said blood pump, and a flow line interconnecting the outlet of said blood pump and an inlet of the oxygenator.

21. An impeller for a liquid pump having an inlet and an outlet, the impeller comprising in combination: an elongated axially extending core, a centrifugal pumping section including a plurality of vanes extending outwardly form the core and being rotatable in a plane for centrifugal pumping of liquid to an outlet of a liquid pump, said vanes including generally planar sections extending at an angle to said plane of rotation, said impeller further including a helical pumping section including a plurality of fingers extending from said vanes respectively along helical paths about said core and towards the inlet and terminating in extremities angularly spaced from each other at the inlet, and wherein said blades merge into said fingers in a plane common to both and without interruption.

22. A liquid pump including a housing, a liquid inlet and a liquid outlet communicating with the interior of the housing, an impeller for pumping liquid from the inlet to the outlet, said Impeller including an elongated axially extending core, a centrifugal pumping section including a plurality of vanes extending outwardly from the core and being rotatable in a plane for centrifugal pumping of liquid to the outlet, said vanes including generally planar sections extending at an angle to said plane of rotation, said impeller further including a helical pumping section including a plurality of fingers extending from said vanes respectively along helical paths about the core and axis of the impeller and towards the inlet and terminating in extremities angularly spaced from each other at the inlet, and wherein said vanes merge into said fingers in a plane common to both and without interruption.

23. The combination defined in claim 1 wherein said means includes a locking member fixed to the motor and having openings receiving locking members on the housing of the blood pump upon rotation of the blood pump relative to the motor.

* * * * *